United States Patent [19]

Peranich

[11] Patent Number: 5,525,521
[45] Date of Patent: Jun. 11, 1996

[54] CYSTIC FIBROSIS TESTER

[75] Inventor: Larry S. Peranich, San Diego, Calif.

[73] Assignee: Borrego Analytical, Inc., San Diego, Calif.

[21] Appl. No.: 490,820

[22] Filed: Jun. 15, 1995

[51] Int. Cl.[6] .................................... G01N 23/02
[52] U.S. Cl. .............................. 436/150; 422/22; 436/63; 436/79; 436/125; 324/639
[58] Field of Search .................................. 422/22, 82.01; 436/63, 79, 125, 150; 324/639

[56]     References Cited

U.S. PATENT DOCUMENTS

| | | |
|---|---|---|
| 4,104,585 | 8/1978 | Schofield . |
| 4,277,741 | 7/1981 | Faxvog . |
| 4,365,303 | 12/1982 | Hannah . |
| 4,381,485 | 4/1983 | Steinbrecher . |
| 4,472,505 | 9/1984 | Manabe . |
| 4,587,624 | 5/1986 | Banno . |
| 4,703,273 | 10/1987 | Kolbe . |
| 4,881,183 | 11/1989 | Groe . |
| 4,884,213 | 11/1989 | Iwata . |
| 4,896,097 | 1/1990 | Berger . |
| 4,990,858 | 2/1991 | Garner . |

*Primary Examiner*—Lyle A. Alexander
*Attorney, Agent, or Firm*—Nydegger & Associates

[57]              ABSTRACT

A device and method for testing for Cystic Fibrosis includes a sample cell having a capillary tube with a lumen that will hold approximately five microliters of sweat. The capillary tube has metallic rings around each end of the tube with an RF oscillator attached to one ring and a microprocessor attached to the other. An RF signal, which is transmitted from the RF oscillator through the sweat in the sample cell, is subsequently analyzed at the microprocessor by comparing the transmitted signal to a reference. In accordance with the comparison made by the microprocessor, the presence of Cystic Fibrosis may be detected.

23 Claims, 2 Drawing Sheets

CYSTIC FIBROSIS TESTER

FIELD OF INVENTION

This invention is in the field of devices which are used to test biological fluids for salinity content. The present invention is particularly, but not exclusively, useful as a test apparatus for determining the salinity content of sweat as an indicator of the presence of cystic fibrosis.

BACKGROUND OF THE INVENTION

Cystic fibrosis is a genetically transmitted disorder that affects infants, children, and young adults. Specifically, cystic fibrosis involves a dysfunction of the exocrine glands and is characterized by symptoms of chronic pulmonary disease, pancreatic deficiency, and high levels of electrolytes in the sweat of the patient. It is generally fatal, and the majority of deaths occur in victims under the age of twenty-five. One out of approximately every two thousand live births in the United States is afflicted with the disorder.

The pulmonary problems associated with cystic fibrosis result from excessive production of mucous in the respiratory tract. These problems can be treated through long term care or lung transplant and thus, early diagnosis can be beneficial in such cases. The pancreatic damage associated with the disorder can be avoided through the use of recently developed therapies, if diagnosis occurs at an early stage. It is obvious, then, that early diagnosis is crucial.

It is known that genetic testing can be used to diagnose cystic fibrosis. There are, however, a number of different genetic mutations that may result which can yield a false positive indication. Consequently, genetic testing does not presently exhibit the necessary reliability for a proper diagnosis. It happens, however, that testing the sweat of the patient provides a more reliable diagnostic result.

Two types of sweat tests are presently available. One type, a wet chemical test for the chloride ion, has the disadvantage of being labor intensive, and therefore, expensive. Further, health care insurers often will not reimburse health care providers fully for the cost of the wet chemical test. In addition, a relatively large amount of sweat is required. The other type of testing available is an electrical conductivity test which uses electrodes to directly measure the ionic concentration of salt in sweat. Currently known conductivity tests which use electrodes, however, suffer from inaccuracies caused by chemical interaction between the electrode surface and the sweat, or by contamination from previous samples. Further, like the wet chemical test, the currently known electrode tests require a relatively large amount of sweat.

A major problem with currently known testing methods is the requirement for collecting a large sample of sweat. Unfortunately, patients who are afflicted with cystic fibrosis are often sick infants or children who may not be able to produce large amounts of sweat. To help resolve this problem, perspiration is sometimes chemically induced in the patient, and the perspiration is then collected from the skin with gauze and transferred to a sample receptacle. In any case, the collection of a sufficient amount of sweat for performance of the known types of tests is very time consuming. Furthermore, a significant number of tests fail or must be repeated because of insufficient sample sizes.

In light of the above, an object of the present invention is to provide a method and apparatus for testing the conductivity of perspiration, which does not require a large amount of sweat, and which does not suffer inaccuracies resulting from chemical interaction between the sweat and electrode surfaces, or carry-over from previous samples. A further object of the present invention is to provide a method and apparatus for testing the conductivity of perspiration, which is easy and economical to use.

SUMMARY OF THE INVENTION

The present invention is a method and apparatus for measuring the conductivity and salt concentration of very small quantities of sweat or other biological fluids. Included in the apparatus is a sample cell which has two metallic rings which are mounted coaxially, and a dielectric spacer separating the two metallic rings axially from each other. A central hole runs through each metallic ring and the dielectric spacer. A capillary tube manufactured of a dielectric material is insertable into the central holes through the metallic rings and the dielectric spacer.

In accordance with the present invention, to test the salinity content of a sweat sample, an electrical signal is passed through the sweat sample. To do this, sweat is collected from the patient and then placed into the capillary tube. The capillary tube is then inserted into the central holes in the metallic rings and the dielectric spacer. The two metallic rings of the sample cell are electrically connected into an electrical test circuit to establish the sweat sample as part of the circuit. An initial electrical signal is imposed on a first ring of the two metallic rings and a resultant electrical signal is received at the second metallic ring. The amplitude of the resultant radio frequency signal measured at the second metallic ring is indicative of the conductivity of the sweat sample in the capillary tube. For the present invention, the initial electrical signal frequency is in the radio frequency range, preferably 10 to 30 MHz.

The apparatus of the present invention also includes a reference circuit which is used to determine the relative magnitude of the resultant signal from the test circuit. For this reference circuit, the radio frequency signal which is imposed on the first metallic ring is fed to a known resistance to yield a known output signal. It is this output signal to which the measured resultant signal from the second metallic ring can be compared. For this comparison, the RF output signals from the reference circuit and the second metallic ring of the sample cell are fed to detector circuits. In the detector circuits, the RF signals are converted to DC signals having amplitudes which vary in a known manner relative to the amplitudes of the RF signals. These DC signals are fed to an analog to digital converter and then to a microprocessor. It is the microprocessor which performs a comparison of the two signals.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF PREFERRED EMBODIMENTS

Figure 1:
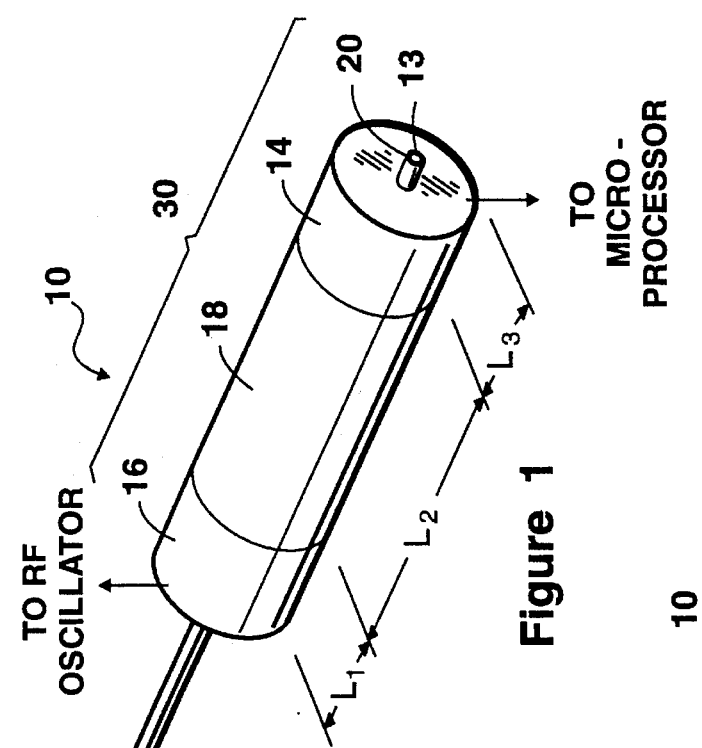
FIG. 1 is a perspective view of a sample cell of the present invention.

As shown in FIG. 1, a sample cell 10 as used in the present invention includes a hollow capillary tube 12 made from a dielectric material, such as glass or a relatively rigid plastic. Capillary tube 12 is approximately 40 millimeters (mm) in length, 0.8 mm in outside diameter, and 0.55 mm in inside diameter. Lumen 13 of this tube 12, if full, would hold a quantity of fluid of up to approximately nine microliters. In actual practice, as will be explained below, the lumen 13 of the capillary tube 12 need only contain sufficient perspiration to fill a sufficient length of the lumen of the tube 12 to perform the conductivity measurement. As a practical matter, a sample size of between one and five microliters will normally be sufficient.

Figure 2:
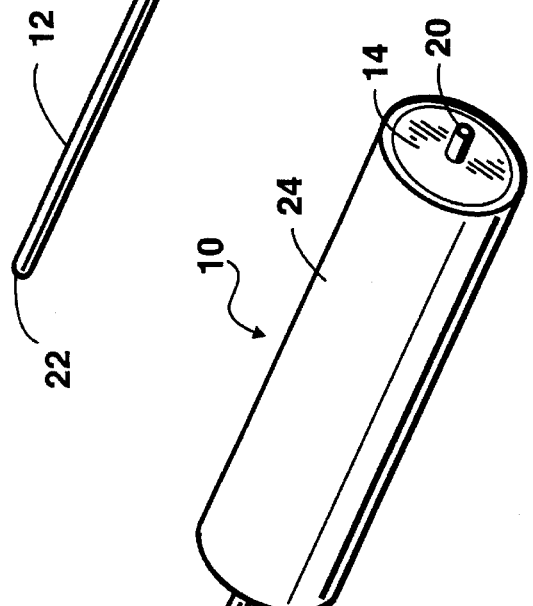
FIG. 2 is a perspective view of the sample cell shown in FIG. 1, without the dielectric spacer.

Sample cell 10 further includes a pair of solid cylindrical metallic rings 14, 16 arranged coaxially around the capillary tube 12. Arrangement of the metallic rings 14, 16 on the capillary tube 12 is shown more clearly in FIG. 2. Metallic rings 14, 16 are made from a conductive material, such as copper, brass, or aluminum. Capillary tube 12 passes through central holes in the rings 14, 16. A sweat sample can be placed within the capillary tube 12, and then the tube 12 can be inserted through the central holes in the rings 14, 16. The sample fluid can be drawn into the capillary tube 12 at a first end 20. The first end 20 of the capillary tube 12 can then be inserted into the rings 14, 16, or slightly beyond.

An oscillating electrical signal is applied to the first ring 14 to induce a current in the sweat sample contained within lumen 13 of the capillary tube 12. The oscillating current in the sweat sample, in turn, induces a measurable oscillating signal in the second ring 16. Rings 14, 16 are separated approximately 10 to 15 millimeters apart. Each gap between the rings 14, 16 and the sweat sample, across the dielectric wall of the capillary tube 12, will have a capacitance. The length $L_1$ of the first ring 14, and the length $L_3$ of the second ring 16 are long enough to cause the capacitance of these gaps to be sufficiently great that the reactance of the gaps is significantly less than the resistance of the sweat sample between the rings 14, 16. The reactance of the gaps should be no more than one tenth the resistance of the sample fluid, to avoid the situation in which slight changes in the reactance due to capillary position variance would introduce a substantial error to the measurement.

Referring again to FIG. 1, the metallic rings 14, 16 are separated by a solid cylindrical dialectric spacer 18. The spacer 18 can be made from a plastic material such as Teflon tetrafluoroethylene polymer, as made by DuPont de Nemours, E. I. and Co. The capillary tube 12 passes through a central hole in the spacer 18. The length $L_2$ of the dialectric spacer 18 is chosen to achieve a desired distance between the metallic rings 14, 16 of from ten to fifteen millimeters. This means that the required sample size is only the amount of fluid sufficient to span the length ($L_2$) of the dielectric spacer 18 and the combined lengths ($L_1$ plus $L_3$) of the metallic rings 14, 16.

Figure 3:
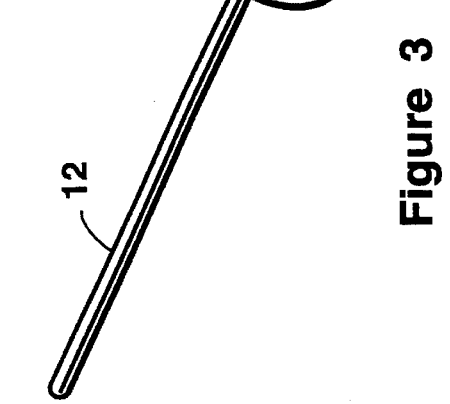
FIG. 3 is a perspective view of the sample cell shown in FIG. 1, with a heat regulating jacket in place.

As shown in FIG. 3, the sample cell 10 preferably has the metallic rings 14, 16 and the dielectric spacer 18 covered by a heat regulating jacket 24. The resistance of the sample fluid will vary according to the temperature of the fluid. Therefore, it is necessary to regulate the temperature of the sample cell 10 at a desired measurement temperature, and to thereby regulate the temperature of the sweat sample to insure reliable results. The jacket 24 can be designed to regulate the temperature of the sample cell 10 and the sweat sample by resistance heating, insulation, or a combination of these or other known temperature regulation techniques.

Figure 4:
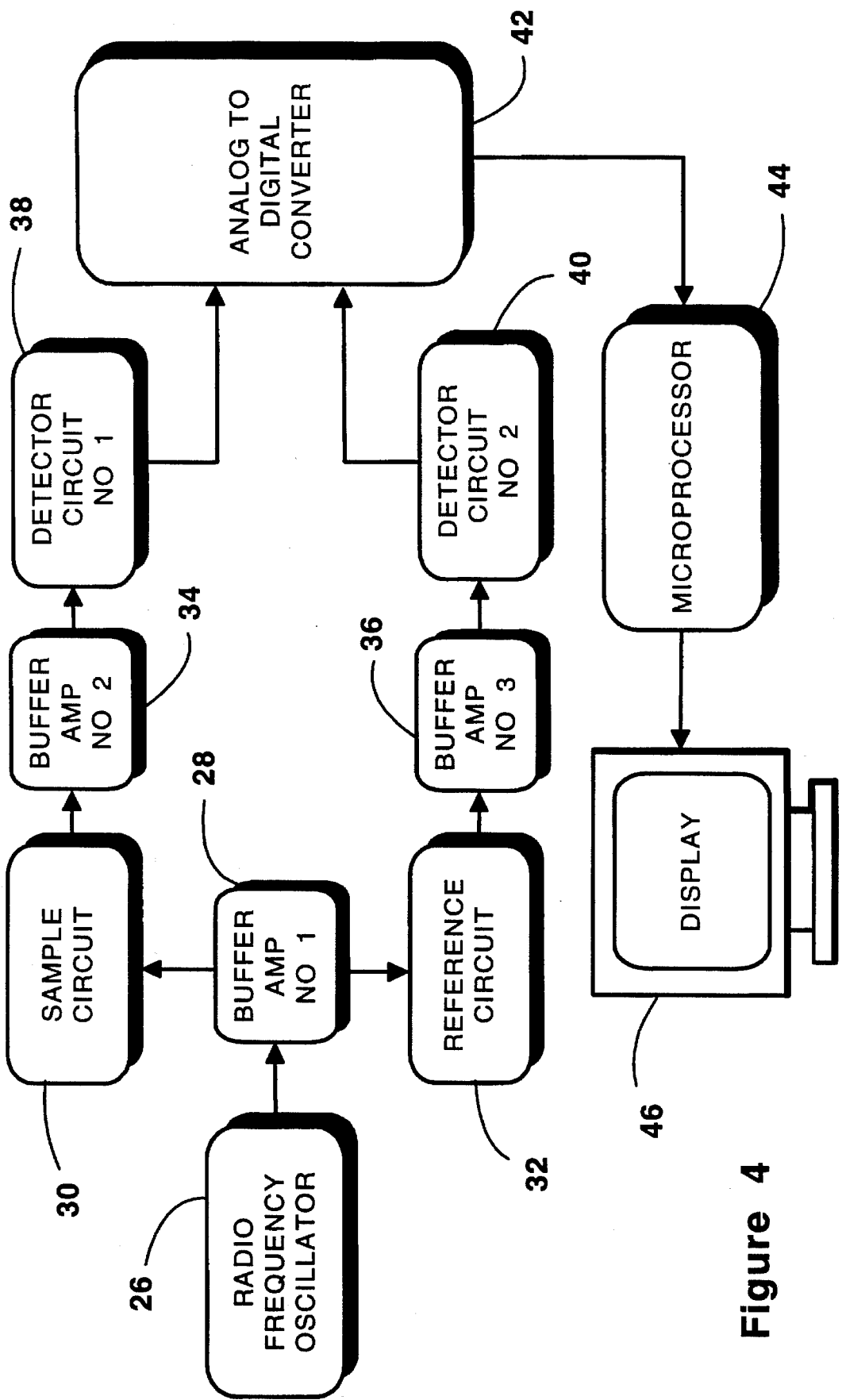
FIG. 4 is a schematic diagram of the conductivity measurement circuit of the present invention.

FIG. 4 shows a schematic diagram of the circuitry by means of which the desired conductivity measurement is taken. The output of a radio frequency oscillator 26, capable of generating a signal with a frequency range of at least ten to thirty megahertz, is connected to a first buffer amplifier 28. The output of the first buffer amplifier 28 is connected to a sample circuit 30 and a reference circuit 32. The sample circuit 30 includes the sample cell 10. Within the sample circuit 30, the generated radio frequency signal is applied to the first metallic ring 14 of the sample cell 10 and the induced radio frequency signal at the second metallic ring 16 of the sample cell 10 is measured. The strength of the induced radio frequency signal varies with the conductivity of the sweat sample. The reference circuit 32 contains a known resistance which provides a reference signal with which the signal from the sample circuit 30 can be compared.

The output from the sample circuit 30 is fed through a second buffer amplifier 34 to a first detector circuit 38. Similarly, the output from the reference circuit 32 is fed through a third buffer amplifier 36 to a second detector circuit 40. The buffer amplifiers 28, 34, 36 used in the circuit are for the purpose of isolating the sample circuit 30 from the reference circuit 32. The first and second detector circuits 38, 40 convert the RF signals into DC signals having amplitudes which vary in a known manner with the amplitudes of the incoming RF signals.

The output signals from the first and second detector circuits 38, 40 are fed through an analog to digital converter 42 to a microprocessor 44. The microprocessor 44 compares the sample signal with the reference signal to determine the conductivity of the sweat sample. The microprocessor 44 can also compute the salinity of the sweat sample, after being calibrated with standard samples. The desired data for conductivity and salinity can be displayed on a device such as a video monitor 46, for the benefit of the user.

OPERATION

A small sample of the patient's perspiration is drawn into the capillary tube 12 of the sample cell 10 through the first end 20 of the tube 12. The first end 20 of the capillary tube 12 is then inserted through the central holes 15, 17 of the first and second metallic rings 14, 16 and the central hole in the dielectric spacer 18. This assembles the sample cell 10. The temperature of the sample cell 10 is maintained at a desired testing temperature by the jacket 24. The radio frequency oscillator 26 imposes a signal having a frequency in the range of ten to thirty megahertz on the first metallic ring 14 of the sample cell 10 and on the reference circuit 32. An induced signal at the second metallic ring 16 of the sample cell 10 yields an output signal from the sample circuit 30. The output signal from the sample circuit 30 and the output signal from the reference circuit 32 are converted to DC signals by first and second detector circuits 38, 40, respectively. The DC output signals of the first and second detector circuits 38, 40 are then converted to digital signals by an analog to digital converter 42. The output of the analog to digital converter 42 is fed to the microprocessor 44, where the conductivity and salinity of the sweat sample in the sample cell 10 are computed. The results are then displayed on the video monitor 46. A new capillary tube is used for each measurement, and discarded afterward. This eliminates the need to clean the system between measurements, and prevents carry-over from previous samples.

While the particular CYSTIC FIBROSIS TESTER and its method of operation as herein shown and disclosed in detail are fully capable of obtaining the objects and providing the advantages herein before stated, it is to be understood that the disclosed method and apparatus are merely illustrative of the presently preferred embodiments of the invention and that no limitations are intended to the details of construction, design, or operation herein described other than as recited in the appended claims.

I claim:

1. A testing device which comprises:
    a capillary tube having a first end and a second end and a lumen extending therebetween, said lumen being dimensioned to hold at least one microliter of biological fluid;
    a first metallic ring surrounding said lumen at said first end;
    a second metallic ring surrounding said lumen at said second end;
    means for transmitting a radio frequency signal within the range of approximately ten to thirty megahertz through said biological fluid in said lumen from said first ring to said second ring;
    means for generating a radio frequency reference signal; and
    means for comparing said radio frequency signal at said second ring with said reference signal to determine salt concentration in the biological fluid.

2. A device as recited in claim 1 wherein said transmitting means is a radio frequency oscillator.

3. A device as recited in claim 1 wherein said capillary tube has a length between said first ring and said second ring, and said length is in the range of approximately ten to fifteen mm.

4. A device as recited in claim 1 wherein said comparing means is a microprocessor.

5. A device as recited in claim 1 further comprising a circuit for establishing said reference signal, said circuit having an input port and an output port with said transmitting means being connected to said input port and said comparing means being connected to said output port.

6. A device as recited in claim 1 further comprising an analog to digital converter, said converter being electrically connected between said second ring of said capillary tube and said comparing means.

7. A device as recited in claim 1 wherein said first ring has a first width and said second ring has a second width, and wherein said first width and said second width establish a capacitance on said tube between said respective ring and said biological fluid in said lumen to create a reactance which is substantially less than the resistance of said biological fluid in said lumen between said first ring and said second ring.

8. A device as recited in claim 1 further comprising a dielectric spacer positioned around said tube between said first ring and said second ring to maintain a predetermined distance therebetween.

9. A device as recited in claim 8 wherein said predetermined distance is in the range of from ten to fifteen mm.

10. A device as recited in claim 8 further comprising means for regulating the temperature of said biological fluid in said lumen to maintain a substantially constant temperature for said biological fluid.

11. A device as recited in claim 10 wherein said first metallic ring and said second metallic ring are respectively attached to said dielectric spacer with said spacer therebetween to form a biological fluid resistance measuring unit.

12. A device as recited in claim 11 wherein said temperature regulating means is a jacket which fits over said measuring unit.

13. A device as recited in claim 12 wherein said spacer is made of teflon.

14. A device as recited in claim 12 wherein said first ring and said second ring are made of a metal consisting of copper, brass or aluminum.

15. A system for analyzing biological fluid which comprises:
    means for holding a sample of biological fluid, said sample being at least one microliter in volume;
    a radio frequency oscillator for transmitting a radio frequency, signal within the range of approximately ten to thirty megahertz through said biological fluid in said holding means; and
    means for comparing said radio frequency signal, after transmission thereof through said biological fluid, with a radio frequency reference signal to determine salt concentration in said biological fluid.

16. A system as recited in claim 15 wherein said holding means comprises:
    a capillary tube having a first end and a second end and a lumen extending therebetween;
    a first metallic ring surrounding said lumen at said first end; and
    a second metallic ring surrounding said lumen at said second end.

17. A system as recited in claim 15 wherein said capillary tube has a length between said first ring and said second ring, and said length is in the range of approximately ten to fifteen mm.

18. A system as recited in claim 15 wherein said comparing means is a microprocessor.

19. A system as recited in claim 15 further comprising:
    a circuit for establishing said reference signal, said circuit having an input port and an output port with said radio frequency oscillator being connected to said input port and said comparing means being connected to said output port; and
    an analog to digital converter, said converter being electrically connected between said holding means and said comparing means.

20. A method for analyzing biological fluids which comprises the steps of:
    placing at least one microliter of biological fluid in the lumen of a capillary tube having a first end and a second end with said lumen extending therebetween, and having a first metallic ring surrounding said lumen at said first end, and a second metallic ring surrounding said lumen;

transmitting a radio frequency signal within the range of approximately ten to thirty megahertz through said biological fluid in said lumen at said second end from said first ring to said second ring;

generating a radio frequency reference signal; and comparing said radio frequency signal at said second ring with said reference signal to determine salt concentration in the biological fluid.

21. A method as recited in claim 20 further comprising the steps of:

using a radio frequency oscillator to transmit said radio frequency signal.

22. A method as recited in claim 21 wherein said comparing step is accomplished using a microprocessor.

23. A method as recited in claim 22 wherein said step of generating said reference signal is accomplished using a circuit having an input port and an output port with said radio frequency oscillator being connected to said input port and said microprocessor being connected to said output port.

* * * * *